US008829914B2

(12) United States Patent
Stearns et al.

(10) Patent No.: US 8,829,914 B2
(45) Date of Patent: Sep. 9, 2014

(54) PHOTO IONIZATION DETECTOR FOR GAS CHROMATOGRAPHY HAVING TWO SEPARATELY IONIZING SOURCES AND METHODS OF USE

(71) Applicant: Valco Instruments Company, L.P., Houston, TX (US)

(72) Inventors: Stanley D. Stearns, Houston, TX (US); Huamin Cai, Houston, TX (US)

(73) Assignee: Valco Instruments Company, L.P., Houston, TX (US)

( * ) Notice: Subject to any disclaimer, the term of this patent is extended or adjusted under 35 U.S.C. 154(b) by 163 days.

(21) Appl. No.: 13/675,727

(22) Filed: Nov. 13, 2012

(65) Prior Publication Data

US 2014/0132277 A1    May 15, 2014

(51) Int. Cl.

| G01N 27/62 | (2006.01) |
| H01J 49/00 | (2006.01) |
| G01N 27/66 | (2006.01) |
| H01J 49/10 | (2006.01) |
| G01N 27/64 | (2006.01) |
| G01N 30/64 | (2006.01) |

(52) U.S. Cl.
CPC .............. *G01N 27/66* (2013.01); *H01J 49/107* (2013.01); *G01N 27/64* (2013.01); *G01N 30/64* (2013.01); *G01N 2030/642* (2013.01)
USPC .......................................... 324/464; 250/285

(58) Field of Classification Search
USPC .......... 324/464, 459; 250/281, 282, 283, 285, 250/299, 300
See application file for complete search history.

(56) References Cited

U.S. PATENT DOCUMENTS

| 2,901,625 | A | 8/1959 | Friedman et al. |
| 4,077,773 | A | 3/1978 | Stearns |
| 4,975,648 | A | 12/1990 | Lawson et al. |
| 5,153,519 | A | 10/1992 | Wentworth et al. |
| 5,317,271 | A | 5/1994 | Wentworth et al. |
| 5,393,979 | A | 2/1995 | Hsi |

(Continued)

FOREIGN PATENT DOCUMENTS

| EP | 0745846 B1 | 4/2003 |
| WO | 9427141 A1 | 11/1994 |
| WO | 2012048308 A2 | 4/2012 |

OTHER PUBLICATIONS

Huamin Cai and Stanley D. Stearns, Dual Discharge Photo Ionization Detector for Gas Chromatography, PITTCON 2010—Exposition for Laboratory Science and Innovation, Feb. 28-Mar. 5, 2010, 11 pages, Orlando, Florida, U.S,A.

(Continued)

*Primary Examiner* — Hoai-An D Nguyen
(74) *Attorney, Agent, or Firm* — Crain, Caton & James, P.C.; James E. Hudson, III (57) ABSTRACT

A detector for gas chromatography using two ionization sources within a single body to separately provide ionization energy to a column gas eluent to provide electrical discharge to two or more collecting electrodes provides improved selectivity and may be so used. Use is made of combined bias/ collecting electrodes. The use of two ionization sources permits generation of two detector outputs from within a common body and of a common constituent flow. The ionization sources and any applicable discharge gas and dopant may be selected based on desired selectivity.

14 Claims, 4 Drawing Sheets

(56) References Cited

U.S. PATENT DOCUMENTS

| | | | |
|---|---|---|---|
| 5,394,090 A | | 2/1995 | Wentworth et al. |
| 5,394,091 A | | 2/1995 | Wentworth et al. |
| 5,394,092 A | | 2/1995 | Wentworth et al. |
| 5,528,150 A | | 6/1996 | Stearns et al. |
| 5,532,599 A | | 7/1996 | Stearns et al. |
| 5,541,519 A | | 7/1996 | Stearns et al. |
| 5,594,346 A | | 1/1997 | Stearns et al. |
| 5,767,683 A | | 6/1998 | Stearns et al. |
| 6,133,740 A | | 10/2000 | Wentworth et al. |
| 6,151,971 A | * | 11/2000 | Lin et al. .................... 73/863.23 |
| 6,313,638 B1 | | 11/2001 | Sun et al. |
| 6,333,632 B1 | | 12/2001 | Yang et al. |
| 6,621,077 B1 | | 9/2003 | Guevremont |
| 6,842,008 B2 | | 1/2005 | Stearns et al. |
| 7,075,445 B2 | * | 7/2006 | Booth et al. ................... 340/630 |
| 7,687,771 B2 | * | 3/2010 | Jolliffe et al. ................. 250/285 |
| 2003/0034781 A1 | | 2/2003 | Abdel-Rahman |
| 2004/0178800 A1 | | 9/2004 | Stearns et al. |
| 2005/0194527 A1 | | 9/2005 | Guevremont et al. |
| 2006/0284103 A1 | | 12/2006 | Syage et al. |
| 2007/0181800 A1 | * | 8/2007 | Jolliffe et al. ................. 250/288 |
| 2011/0018546 A1 | | 1/2011 | Kitano et al. |
| 2012/0025070 A1 | | 2/2012 | Miller et al. |

OTHER PUBLICATIONS

Lee W. Young, Notification of Transmittal of the International Search Report and the Written Opinion of the International Search Authority, or the Declaration—PCT/US13/69426, Mar. 19, 2014, 1 page, United States Patent & Trademark Office as International Search Authority, Alexandria, Virginia, United States.

Lee W. Young, International Search Report—PCT/US13/69426, Mar. 19, 2014, 3 pages, United States Patent & Trademark Office as International Search Authority, Alexandria, Virginia, United States.

Lee W. Young, Written Opinion of the International Searching Authority—PCT/US13/69426, Feb. 17, 2014, 5 pages, United States Patent & Trademark Office as International Search Authority, Alexandria, Virginia, United States.

International Search Report—PCT/US13/69426—Search History, Feb. 17, 2014, 18 pages, United States Patent & Trademark Office as International Search Authority, Alexandria, Virginia, United States.

* cited by examiner

PHOTO IONIZATION DETECTOR FOR GAS CHROMATOGRAPHY HAVING TWO SEPARATELY IONIZING SOURCES AND METHODS OF USE

CROSS-REFERENCE TO RELATED APPLICATIONS

None.

STATEMENT REGARDING FEDERALLY SPONSORED RESEARCH OR DEVELOPMENT

Not Applicable.

BACKGROUND OF THE INVENTION

1. Field of Invention

An improvement to ionization detectors for gas chromatography and methods of use is disclosed. More specifically, a detector for gas chromatography with two separate ionization sources within a single body to separately provide ionization energy to, via a discharge gas, permit ionization of a column gas eluent to provide electrical discharge to two or more collecting electrodes, which may be combined bias/collecting electrodes, and methods of use provides improved selectivity, is disclosed.

2. Description of the Related Art

Gas chromatograph systems used to detect the presence of specific compounds include the well-known use of ionization detectors. A sample is vaporized and introduced to the head of a gas chromatographic column, where it is transported through the column by the flow an inert, gaseous mobile phase, and is separated according to physical properties of each compound in the sample. The eluent from this gas chromatography column is then flowed into the enclosed elongated chamber of an ionization detector. Helium, or another noble gas, or combinations thereof, is also introduced to the detector as a discharge gas and is ionized in a discharge chamber section of that enclosed elongated chamber, wherein energy is absorbed and the atoms transition to an exited state. The ion combine with another atom to form a diatomic metastable molecule, which then emits emitting a molecule emission—one or more photons. In an adjacent reaction chamber section of the enclosed elongated chamber, the separated constituents or compounds, in accordance with their retention time in the column, become ionized from photons emitted from the ionized discharge gas, each according to its composition. As each ionized compound encounters a collecting electrode, an electrical current is generated, which is useful, as more than one compound can have the same or similar retention times, in identification of each compound in the sample according to its ionization potential (IP) and retention time. Various benefits of this non-destructive nature of this detection have been identified.

Variations of the means of ionization of the discharge gas exist, including those which use an electric discharge, whether a direct current discharge (a pulsed discharge) or an alternating current discharge, others which use a dielectric barrier discharge, and others which use a lamp. Each ionization source provides its own benefits. The pulsed discharge detector (PDD), for example, has the advantages of stability and long lifetime. These detectors have been found useful in various areas, including trace gas analysis, semiconductor manufacturing, and environmental applications.

These detectors have used a single collecting electrode, which may be part of a system including at least one bias electrode, or may use a single combination bias/collecting electrode, where the collecting electrode is itself biased. Unfortunately, use of a single collecting electrode limits the information which may be obtained from within the detector cell. Moreover, these systems are non-selective, as they respond to all compounds except the carrier gas. While several methods for improving selectivity have been published, these have not been found sufficiently successful for adoption. Among these attempts has been the use of operating two separate gas detectors, each with a different discharge gas type, in parallel, using a division of the eluent from the gas chromatography column into each detector. Splitting the eluent, however, can create difficulties in ensuring an equal division of compounds between the two associated detectors. Moreover, the two detectors may produce differing results, such as by the result of contamination or deterioration of the detector components, which cannot be addressed by reference to a standard.

Thus, there is a need in the art for a photo ionization detector for gas chromatography with increased selectivity which features within a common body two separate ionization discharge locations which separately ionize an undivided eluent, and for methods of use thereof.

SUMMARY OF THE INVENTION

The present photo ionization detector uses two separately ionizing discharge sources and two or more combined bias/collecting electrodes. In operation, the use of two ionization sources permits generation of two detector outputs. The ionization sources and any applicable discharge gas and dopant may be selected based on desired selectivity.

The present photo ionization detector provides a dual ionization source ionization detector body which includes an elongated chamber, a first ionization source, a column gas inlet, a second ionization source, an outlet, a first combined bias/collecting electrode, and a second combined bias/collecting electrode. The extent of the enclosed elongated chamber is defined by a first end and a second end. The first ionization source is positioned within the enclosed elongated chamber adjacent or at the first end, while the second ionization source is positioned within the enclosed elongated chamber adjacent or at the second end. The column gas inlet, through one side of the detector body, which may be positioned in the enclosed elongated chamber between the first ionization source and the chamber second end, provides an entrance into the enclosed elongated chamber between the first ionization source and the second end, while the outlet is positioned to provide an exit from the enclosed elongated chamber between the point of entry of the column inlet and the second ionization source. An end of the first collecting electrode is exposed in the enclosed elongated chamber between the column gas inlet and the outlet. An end of the second collecting electrode is exposed in the enclosed elongated chamber between the end of the first collecting electrode and the second ionization source. In an embodiment using pulsed discharge ionization as the first ionization source, the photo ionization detector also includes a first discharge gas inlet through the wall of the detector body and into the enclosed elongated chamber, near the chamber first end, so that the first ionization source is positioned between the first discharge gas inlet and the chamber second end. The end of the second collecting electrode may be positioned between the end of the first collecting electrode and a second gas discharge gas inlet, if the second ionization source is pulsed discharge. Finally, the outlet may be positioned between the end of the second collecting electrode and the chamber.

In operation, the photo ionization detector may be utilized in a method of identifying separated constituents in a carrier gas. The separated constituents in a carrier gas are flowed from a column gas inlet into the enclosed elongated chamber, where they are ionized by photon emission from the first discharge gas, which has been ionized by the first ionization source, and by photon emission from the second discharge gas, which has been ionized by the second ionization source. By interaction with the ionized constituents, over time, a first time-dependent current is generated in the first collecting electrode and a second time-dependent current is generated in the second collecting electrode. The separated constituents are then flowed out of the detector body through the outlet. A visual representation of the first and second time dependent currents may then be displayed as a function of time, either directly or relation to one another.

A photo ionization detector using two separate ionization source, such as dual discharge sources, and with two or more collecting electrodes provides improved selectivity. Beneficially, in use, the response ratio between any two collecting electrodes provides confirmation of the compound identities indicated by the retention time. Moreover, the photo ionization detector using dual discharge sources and multiple collecting electrodes retains the universal and uniform response characteristics of a conventional photo ionization detector without the need for a second detector or for division of the effluent from the gas chromatography column.

Using helium doped with argon, krypton, or xenon as the second discharge gas rather than pure helium provides a simultaneous, but different, discharge emission profile. Pure helium provides higher photon energy, ionizing compounds in the eluted sample. Use of a dopant results in a reduction in the photon energy, thus ionizing only selected components. Doped helium is used rather than a pure non-helium gas in order to retain the benefits of the helium: namely, its transparency for Ar, Kr, and Xe resonance radiation and its efficient cooling of the electrodes. Moreover, the photo ionization detector using a second discharge source with such doped discharge gas provides the simultaneous functionality of a specific photoionization detector for selective determination of aliphatics, aromatics, amines, and other species. For example, use of Argon provides selectivity for organic compounds, use of Kypton provides selectively for unsaturated compounds, and use of Xenon provides selectivity for polynuclear aromatics.

Bias electrodes, biased by a voltage source may also be included in the detector body, but increase the number of components required.

Finally, determination of the ratio of the Ionization Potential for each compound within the sample, made possible from the dual discharge locations and multiple collecting electrodes, aids in identification of the compound.

Additional aspects, advantages, and embodiments of the photo ionization detector will become apparent to those skilled in the art from the following description of the various embodiments and related drawings.

BRIEF DESCRIPTION OF THE DRAWINGS

So that the manner in which the described features, advantages, and objects of the photo ionization detector, as well as others which will become apparent, are attained and can be understood in detail; more particular description of the photo ionization detector briefly summarized above may be had by referring to the embodiments thereof that are illustrated in the drawings, which drawings form a part of this specification. It is to be noted, however, that the appended drawings illustrate only typical embodiments of the photo ionization detector and are therefore not to be considered limiting of its scope as the photo ionization detector may admit to other equally effective embodiments.

In the drawings.

DESCRIPTION OF THE PREFERRED EMBODIMENT

The present photo ionization detector provides a detector body for dual discharge photo ionization detector with two or more collecting electrodes and a method of use for gas chromatography.

Figure 1:
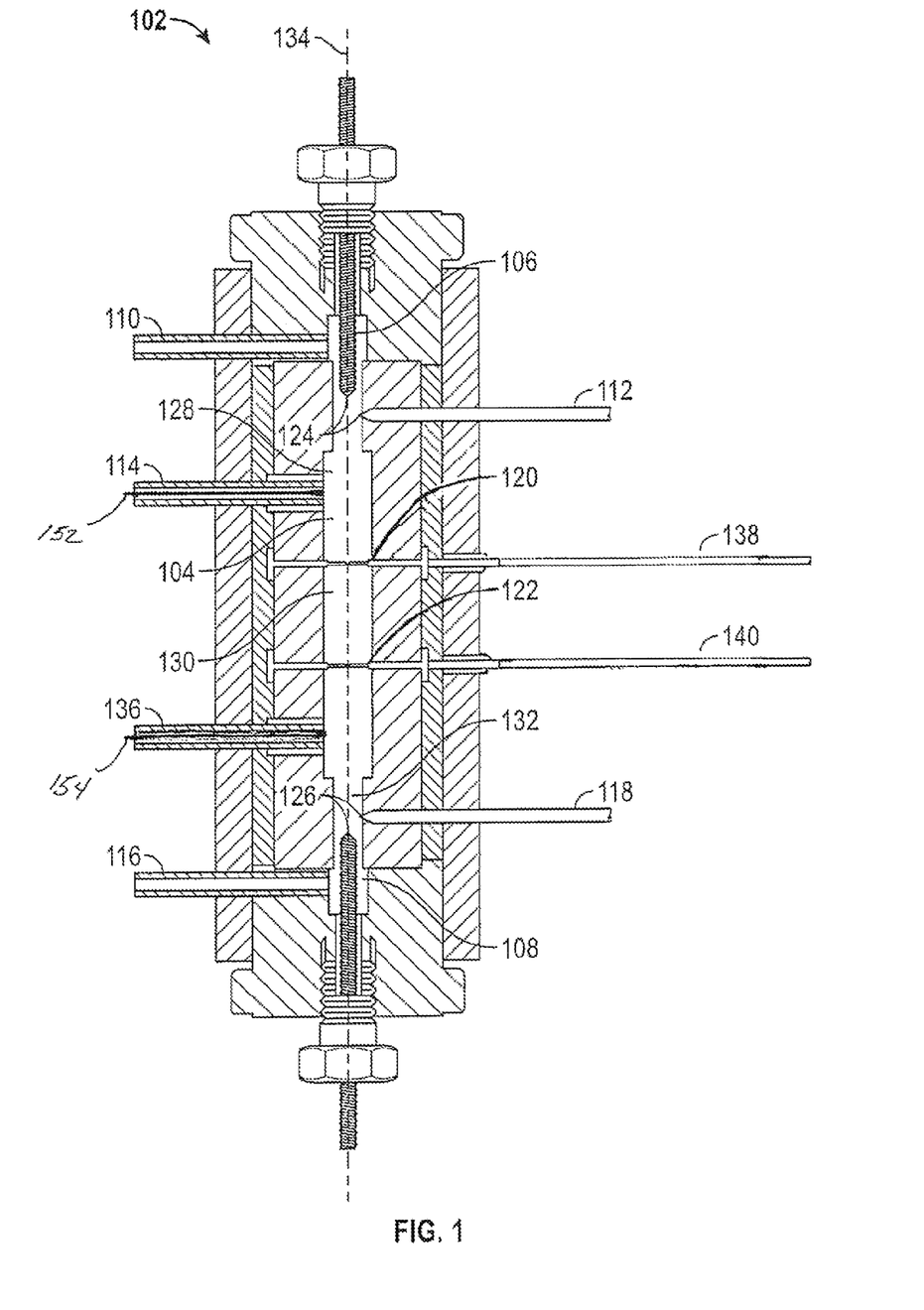
FIG. 1 is an illustration of a detector body of the present photo ionization detector using pulsed discharge as the first and second ionization sources.

Referring to FIG. 1, an illustration of a detector body of the present photo ionization detector using pulsed discharge as the first and second ionization sources, the dual ionization source ionization detector body 102 includes an enclosed elongated chamber 104 having a chamber first end 106 and a chamber second end 108, a first ionization source 112, a second ionization source 118, a column gas inlet piping 114, a first collecting electrode 138 having a first collecting electrode end 120 which may be constructed to function as a combined bias/collecting electrode, and a second collecting electrode 140 having a second collecting electrode end 122 which may be constructed to function as a combined bias/collecting electrode, and an outlet piping 136 from the enclosed elongated chamber 104. The detector body may further include a first discharge gas inlet 110 and a second discharge gas inlet 116. The first discharge gas inlet 110 may be positioned into or at the enclosed elongated chamber 104 proximate, i.e at or near, the chamber first end 106. The second discharge gas inlet 116 may be positioned into or at the enclosed elongated chamber 104 proximate, i.e at or near, the chamber second end 108. The first discharge gas inlet 110 may therefore provide a pathway into the enclosed elongated chamber 104 proximate the chamber first end 106 for a first discharge gas while the second discharge gas inlet 116 provides a pathway into the opposing end of enclosed elongated chamber for a second discharge gas proximate the chamber second end 108. The first ionization source 112 is positioned in the enclosed elongated chamber 104 adjacent the chamber first end 106 and, in operation, downstream of the first discharge gas inlet 110 while the second ionization source 118 is positioned in the enclosed elongated chamber 104 adjacent said chamber second end 108, which, in operation, will also be downstream of the second discharge gas inlet 116. As can be appreciated, this positions, in operation, the first ionization source 112 downstream of the first discharge gas inlet 110 and the second ionization source 118 downstream of the second discharge gas inlet 116. The column gas inlet piping 114 is positioned between the first ionization source 112 and the second ionization source 118. This further positions, in operation, the column gas inlet piping 114 downstream of the first discharge gas inlet 110. In operation, the column gas inlet piping 114 provides a pathway into the enclosed elongated chamber 104, which should be positioned closer to first ionization source 112 than the second ionization source downstream of the first ionization source 118. The first collecting electrode end 120 is exposed to the enclosed elongated chamber 104 and, in operation, downstream, with respect to the first discharge gas, of the column gas inlet piping 114 and the first discharge gas inlet 110, thus between the column gas inlet piping 114 and the outlet piping 136. The second collecting electrode end 122 is exposed to the enclosed elongated chamber 104 and, in operation, positioned downstream, with respect to the first discharge gas, of the column gas inlet piping 114, the first discharge gas inlet 110, and the first collecting electrode end 120, so as to be between the first collecting electrode 138 and the second discharge gas inlet 116, when present. The first ionization source 112 may be between the first collecting electrode end 120 and the second ionization source 118. The outlet piping 136 is positioned in or at the enclosed elongated chamber 104, which should be between the second ionization source 118, such as the second pair of spaced-apart electrode tips 126, and the second collecting electrode end 122, and therefore the column gas inlet piping 114. The column gas inlet piping 114 and the outlet piping 136 are hollow and/or cylindrical tubing.

Further, a first biasing-or-ground electrode 152 is positioned in the column gas inlet piping 114 so its end is at least adjacent, i.e., in or at the edge, of the enclosed elongated chamber 104. Similarly, a second biasing-or-ground electrode 154 is positioned in the outlet piping 136 so its end is at least adjacent, i.e., in or at the edge of, the enclosed elongated chamber 104.

Described with reference to the position of the components, the dual ionization source ionization detector body 102 first includes an enclosed elongated chamber 104 having a chamber first end 106 and a chamber second end 108. A first discharge gas inlet 110 provides an inlet into the enclosed elongated chamber 104 near, which necessarily includes at, adjacent to and abutting, the chamber first end 106. A second discharge gas inlet 116 provides an inlet into the enclosed elongated chamber 104 near the chamber second end 108. A first ionization source 112 is positioned in or about the enclosed elongated chamber 104 adjacent the chamber first end 106 and/or between the first discharge gas inlet 110 and the chamber second end 108 so as to provide ionization energy into the enclosed elongated chamber. A column gas inlet piping 114 provides an inlet from a gas chromatography column into the enclosed elongated chamber 104 between the first ionization source 112 and the chamber second end 108 through the wall of the side of the detector body 102. A first collecting electrode end 120 is exposed to the enclosed elongated chamber 104 between the column gas inlet piping 114 and the chamber second end 108. A second collecting electrode end 122 is exposed to the enclosed elongated chamber 104 between the first collecting electrode end 120 and second ionization source 118 or the chamber second end 108 and/or adjacent the chamber second end 108. An outlet piping 136, to provide venting or outflow from the enclosed elongated chamber 104 is positioned in the elongated chamber 104 between the second collecting electrode end 122 and chamber second end 108, or more narrowly, the second discharge gas inlet 116. Finally, a second ionization source 118 is positioned in the enclosed elongated chamber 104 between the outlet piping 136 and the chamber second end 108. The dual ionization source ionization detector body 102 may be further defined by the first discharge gas inlet 110 being positioned in the enclosed elongated chamber 104 near the chamber first end 106, and the chamber second end 108 being positioned in the enclosed elongated chamber 104 near the chamber second end 108.

The chamber 104 may have a chamber first end 106 and a chamber second end 108. The first discharge gas inlet 110 may be positioned proximate, that is on, at, abutting, is close proximity, near, or adjacent to, the chamber first end 106. The second discharge gas inlet 116 may be positioned proximate, that is on, at, near, or adjacent to, the chamber second end 108.

The flow rates associated with the first discharge gas inlet 110 and the second discharge gas inlet 116 need not be equivalent, but provide better results when non-equivalent. The outlet piping 136 has a sufficient flow rate for outflow, whether by size or pressure differential, to permit outflow at a rate equivalent to the inflow at both the first discharge gas inlet 110 and the second discharge gas inlet 116.

The first ionization source 112 and the second ionization source 118 use ultraviolet light (photons) to ionize gas atoms. The discharge of ultraviolet light may be may be obtained by various technology known in the art. These include electrical discharge, particularly generation of an electrical spark between two electrodes as well as ultraviolet lamps, also known as glow-discharge lamps, wherein typically a lamp is filled with a low-pressure inert gas, which when energized, such as by electrodes within the lamp or by an external radiation source produces ultraviolet spectral radiation. In the case of electrical discharge, the wavelength of the emitted photos is dependent on the discharge gas flowing about the discharge. In the case of the glow-discharge lamp, the wavelength is determined by the gas in the lamp. For example, when excited krypton will emit 123.9 nm and 116.9 nm radiation, or the equivalent of 10 eV and 10.6 eV. In the case of electrical discharge, the wavelength of the emitted photos is dependent on the discharge gas flowing about the discharge. In the case of the glow-discharge lamp, the wavelength is determined by the gas in the lamp. For example, when excited krypton will emit 123.9 nm and 116.9 nm radiation, or the equivalent of 10 eV and 10.6 eV. The first ionization source 112 and the second ionization source 118 need not be of an identical type of ionization source and, depending on first discharge gas and second discharge gas selected, need not be of equivalent energies.

The first discharge gas may be helium while the second discharge gas is selected, in connection with the second ionization source 118, to transmit lower photonic energy. This may be accomplished by doping pure helium with a second noble gas, such as Argon, Kypton, Neon and Xenon, in connection with electrical pulsed discharge or by using pure helium with a ultraviolet radiating lamp. Utilizing a different type of ionization source for the second ionization source 118 permits operation of the detector body with a single discharge gas source, particularly helium, and therefore eliminating the need for a second discharge gas source and the associated equipment.

As depicted in FIG. 1, the first ionization source 112 may be a pulsed discharge system, and may include a first pair of spaced-apart discharge electrode tips 124, positioned sufficient for spark formation therebetween within the enclosed elongated chamber 104 for pulsed discharge. Likewise, the second ionization source 118 may also be a pulsed discharge system, which may include a second pair of spaced-apart discharge electrode tips 126, positioned sufficient for spark formation therebetween within the enclosed elongated chamber 104 for pulsed discharge, in which case the discharge gas would be helium with a dopant.

The enclosed elongated chamber 104 may be divided to include a first ionization chamber section 128, a reaction chamber section 130 and a second discharge chamber section 132, and may be have an enclosed elongated chamber longitudinal axis 134. The first discharge chamber section 128 is located between the chamber first end 106 and the column gas inlet piping 114. The first discharge section 128 may be further identified according to its first discharge chamber section cross sectional area perpendicular to the enclosed elongated chamber longitudinal axis 134, which is generally constant throughout the first discharge chamber section.

Similarly, the second discharge chamber section 132 is located between the chamber second end 108 and the outlet piping 136. The second discharge section 128 may also be further identified according to its second discharge chamber section cross sectional area perpendicular to the enclosed elongated chamber longitudinal axis 134, which is generally constant throughout the second discharge chamber section. The second discharge chamber section cross sectional area should be equivalent to the first discharge chamber section cross sectional area.

While the reaction chamber section 130 intermediate the first discharge chamber section 128 and the second discharge chamber section 132 may have a reaction chamber section cross sectional area perpendicular to the enclosed elongated chamber longitudinal axis 134 equivalent to the first discharge chamber section cross sectional area or the second discharge chamber section cross sectional area, the reaction chamber section cross sectional area should be greater than the first discharge chamber section cross sectional area or the second discharge chamber section cross sectional area.

The first collecting electrode end 120 may be the end of a first collecting electrode 138, which is a combined voltage-biased bias/collecting electrode in electrical connection with a first voltage bias source and for transmittal of the current collected at the first collecting electrode 138. Similarly, the second collecting electrode end 122 may be the end of a second collecting electrode 140, which is a combined voltage-biased bias/collecting electrode in electrical connection with a second voltage bias source and for transmittal of the current collected at the second collecting electrode 140.

Figure 2:
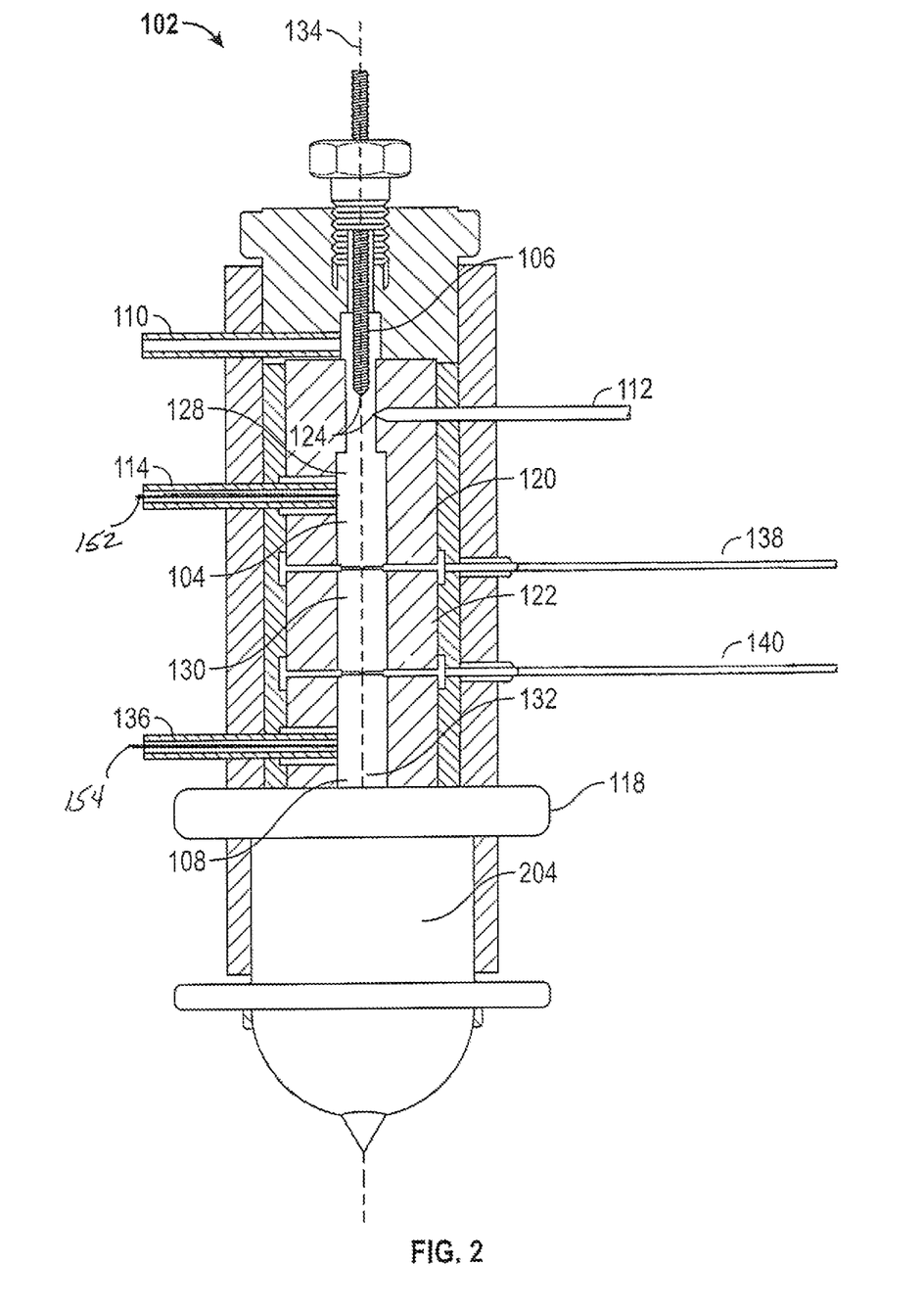
FIG. 2 is an illustration of a detector body of the present photo ionization detector using pulsed discharge as the first ionization source and a lamp as the second ionization source.

Referring to FIG. 2, an illustration of a detector body of the present photo ionization detector using pulsed discharge as the first ionization source and a lamp as the second ionization source, the general structure of the detector body 102 is maintained with changes pertinent to selection of a glow-discharge lamp 204 as the second ionization source 118. As the glow-discharge lamp, positioned at the chamber second end 108, contains the second discharge gas, no second discharge gas inlet 116 is needed.

By virtue of this structure, two chromatograms may be generated in operation, differing as a result of the differing ionization energy transmitted from the two discharge gases and the responses generated from different constituent compounds in the sample. A current of higher intensity will be generated in the first collecting electrode 138 at its first collecting electrode end 120. This higher intensity current is due to the interaction of the sample compounds and the ionized pure helium used in the first discharge chamber section 128, which produced higher ionization energy. Conversely, a current of lower intensity will be generated in the second collecting electrode 140 at its second collecting electrode end 122. This lower intensity current is due to the interaction of the sample compounds and the ionized noble gas combination used in the second discharge chamber section 132, which produced lower ionization energy. Notably, while this structure provides a higher intensity for each electrode, some constituent compounds in the sample exhibit different responses, such as substantially increased peaks, to the two different ionization levels.

Thus, in operation using dual pulsed discharge ionization sources, helium is flowed through the first discharge gas inlet 110 into the first discharge chamber section 128 at the chamber first end 106 of the enclosed elongated chamber 104 while a combination of helium and a second noble gas is flowed through the second discharge gas inlet 116 into the second discharge chamber section 132 at the chamber second end 108 of the enclosed elongated chamber 104 in an opposing direction of the helium and therefor towards it. The helium is ionized in the first discharge chamber section 128 as it passes the first ionization source 112 while the combination of helium and a second noble gas, a noble gas combination) is ionized in the second discharge chamber section as it passes the second ionization source 118. A carrier gas with sample compounds or constituents (also known as an analyte) is introduced into the enclosed elongated chamber 104 through the column gas inlet piping 114, associated with a gas chromatography column which has already separated the various compounds or constituents of the sample according to various properties of each, and which thereby flows counter to the flow of the two discharge gases. The sample compounds are ionized by the photons emitted by the ionized helium and by the ionized noble gas combination. As the column gas approaches the first collecting electrode end 120 its compounds are ionized by the photons according to the ionization potential of each. As each ionized compound passes the first collecting electrode end 120 an electric current is generated. The retention time and intensity of each current discharge is indicative of the compound. As the column gas approaches the second collecting electrode end 122 its compounds are now ionized by the ionized noble gas combination, having lower ionization energy, according to the IP of each. As each ionized compound passes the second collecting electrode end 122 a second electric current is generated. The retention time and intensity of each current discharge in this second current, represented as a peak on a chromatogram, is also indicative of the compound.

The response from the first collecting electrode 138 and the response from the second collecting electrode 140 are then used for identification. A chromatogram for each collecting electrode may be generated by displaying, by printing or by depiction on a computer screen, the collected current intensity in relation to retention time.

Figure 3:
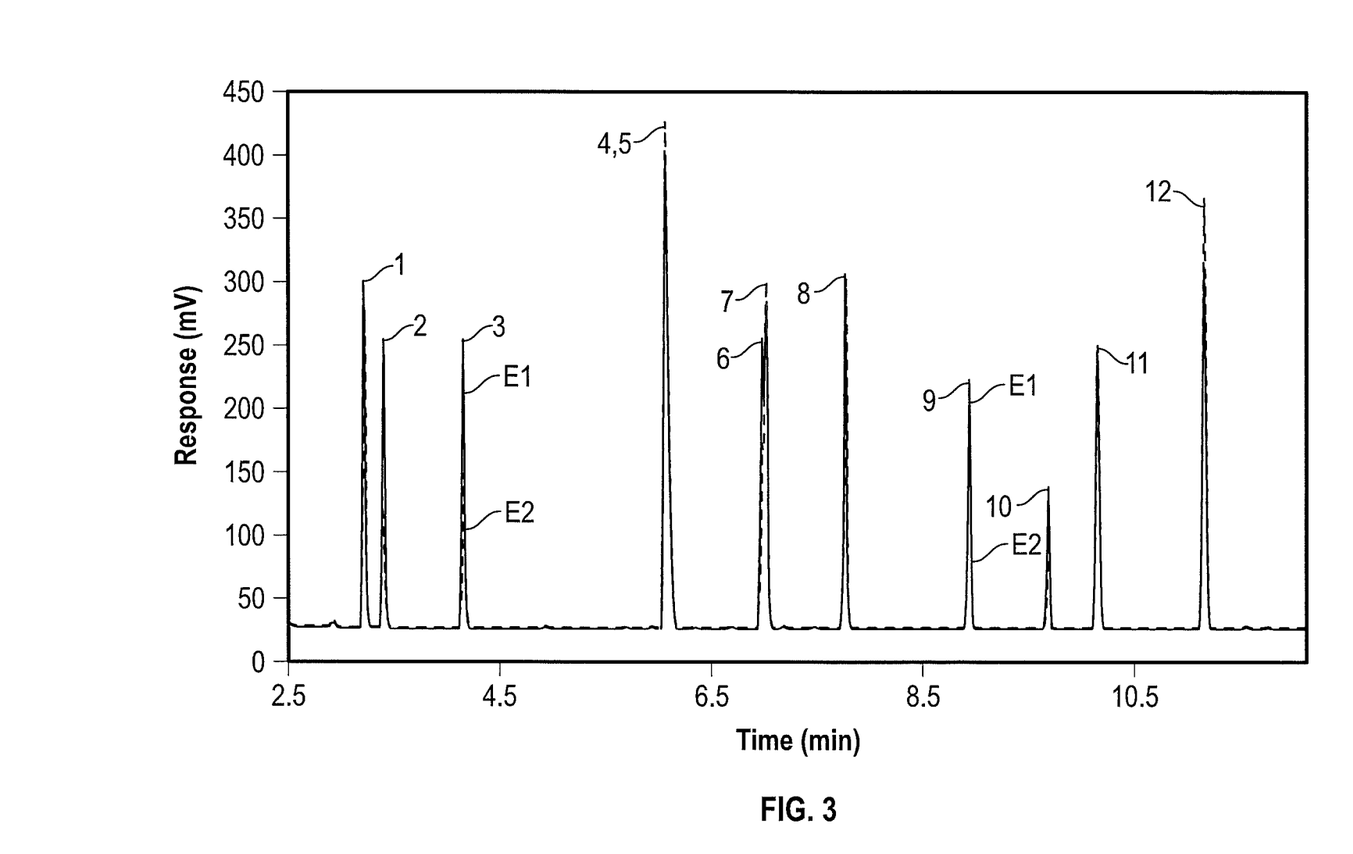
FIG. 3 is an illustration of the operation of the present photo ionization detector, showing current intensities as a function of retention time of the first collected current (E1) at the first collecting electrode 138 and the second collected current (E2) at the second collecting electrode 140 during operation of the present photo ionization detector with helium as a first discharge gas at the first discharge inlet 110 with krypton as a second discharge gas at the second discharge inlet 116 with operation of and the first ionization source 112 and the second ionization source 118, showing the results at the first collecting electrode 138 and at the second collecting electrode 140.

Referring to FIG. 3 and Table 1, two chromatograms generated by the operation of the present photo ionization detector are illustrated, showing current intensities as a function of retention time of the first collected current (E1) at the first collecting electrode 138 and the second collected current (E2) at the second collecting electrode 140 during operation of the present photo ionization detector with helium as a first discharge gas at the first discharge inlet 110 with krypton as a second discharge gas at the second discharge inlet 116 with operation of and the first ionization source 112 and the second ionization source 118, showing the results at the first collecting electrode 138 and at the second collecting electrode 140. The constituents associated with each peak and associated data are presented in Table 1.

TABLE 1

| Peak No. | Constituent | eV |
| --- | --- | --- |
| 1 | 1,1-dichloroethene | 9.79 |
| 2 | methylene chloride | 11.32 |
| 3 | 1,1-dichloroethane | 11.06 |
| 4 | benzene | 9.26 |
| 5 | carbon tetrachloride | 11.47 |
| 6 | 1,2-dichloropropane | 10.87 |
| 7 | trichloroethene | 9.47 |
| 8 | 2-chloroethyl vinyl ether | |
| 9 | 1,1,2-trichloroethane | 11 |
| 10 | Dibromochloromethane | 10.59 |
| 11 | Tetrachloroethene | 9.32 |
| 12 | Chlorobenzene | 9.06 |

Figure 4:
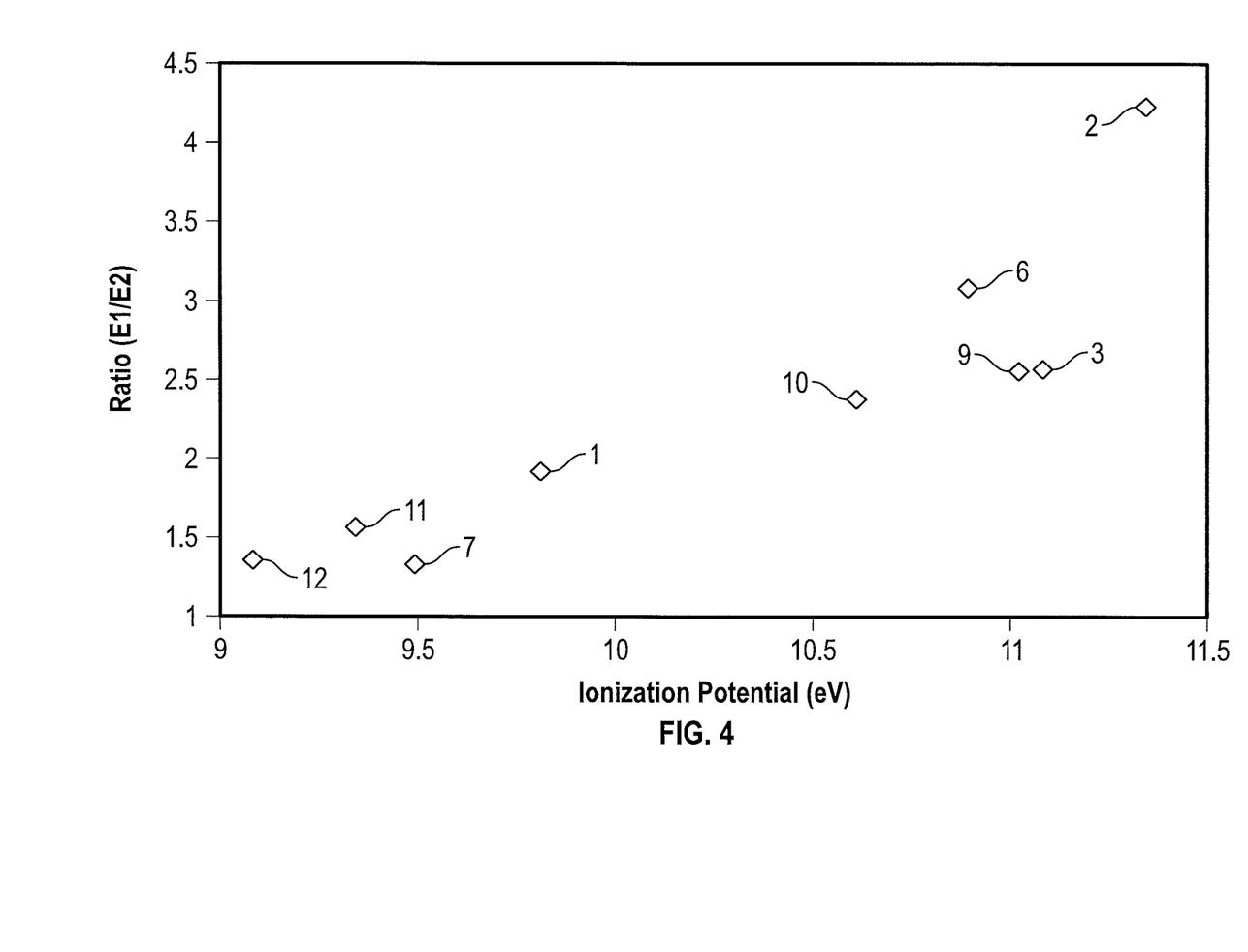
FIG. 4 is an illustration of the ratios of various peaks according to FIG. 3c.

Referring to FIG. 4, a ratio of the first collected current (E1) to the second collected current (E2) may be determined and used in identification, as depicted in Table 2.

TABLE 2

| Peak No. | | eV | E1 | E2 | E1/E2 |
| --- | --- | --- | --- | --- | --- |
| 1 | 1,1-dichloroethene | 9.79 | 509 | 311 | 1.6367 |
| 2 | methylene chloride | 11.32 | 458 | 108 | 4.2407 |
| 3 | 1,1-dichloroethane | 11.06 | 498 | 193 | 2.5803 |
| | benzene | 9.26 | overlap | | |
| | carbon tetrachloride | 11.47 | overlap | | |
| 6 | 1,2-dichloropropane | 10.87 | 517 | 167 | 3.0958 |
| 7 | trichloroethene | 9.47 | 547 | 408 | 1.3407 |
| | 2-chloroethyl vinyl ether | | 620 | 380 | 1.6316 |
| 9 | 1,1,2-trichloroethane | 11 | 467 | 182 | 2.5659 |
| 10 | Dibromochloromethane | 10.59 | 277 | 116 | 2.3879 |
| 11 | Tetrachloroethene | 9.32 | 537 | 341 | 1.5748 |
| 12 | Chlorobenzene | 9.06 | 714 | 523 | 1.3652 |

Referring to Table 2 as depicted in FIG. 4, the response ratio (E1/E2), which covers a wide concentration range, may be used to confirm the compound identifies indicated by the retention time. While the response ratio varies with the intensities of the first ionization source 112 and the second ionization source 118, and with the geometry of the ionization detector body 102, namely the distance between the ionization source 112, 118 and the end 120, 122 of the respective collecting electrode 138, 140, these characteristics are generally fixed. Beneficially, the response ratio is independent of flow, temperature and concentration changes. The variance due to intensities of the first ionization source 112 and the second ionization source 118 may be eliminated by normalizing the values to a known standard, such as benzene. The scale factor necessary for normalizing may be obtained by dividing the ionization potential for benzene according to the second collecting electrode 140 by the ionization potential for benzene according to the first collecting electrode 138. The response ratio for a compound, whether normalized or not, is basically dependent on the Ionization Potential of the compound and its structure, as illustrated in FIG. 4.

The constituents in a sample may thus be identified by providing a detector according to the structure provided above, flowing discharge gases and the sample therethrough and displaying or visually representing to the user the results on a computer screen, or printer, or other display options perceivable by the user. This may be accomplished by providing an enclosed elongated chamber, the chamber having a first end and a second end; providing a first discharge gas inlet into the enclosed elongated chamber proximate the chamber first end; providing a first ionization source, the first ionization source positioned in the enclosed elongated chamber downstream of the first discharge gas inlet; providing a column gas inlet into the enclosed elongated chamber downstream of the first ionization source; providing a second discharge gas inlet into the enclosed elongated chamber proximate the chamber second end; providing a second ionization source, the second ionization source positioned in the enclosed elongated chamber downstream of the second discharge gas inlet; providing an outlet from the enclosed elongated chamber positioned between the column gas inlet and the second ionization source; providing a first collecting electrode end in the enclosed elongated chamber and downstream of the column gas inlet and between the column gas inlet and the outlet; and providing a second collecting electrode end in the enclosed elongated chamber and between the first collecting electrode end and the second ionization source and, when the second ionization source 118 is pulsed discharge, downstream of the second discharge gas inlet. The relevant gases may be flowed through the detector and the electrical output obtained. This includes flowing helium through the first discharge gas inlet into the enclosed elongated chamber; ionizing the flowing helium, the first discharge gas, as it passes the first ionization source to generate photons; flowing a combination of helium and a second noble gas through the second discharge gas inlet into the enclosed elongated chamber; ionizing the flowing combination of helium and a second noble gas, the second discharge gas, as it passes the second ionization source to generate an ionized noble gas combination; flowing a carrier gas and sample compounds mixed therewith through the column gas inlet into the enclosed elongated chamber for exposure to the photons to generate high-ionized sample compounds and for exposure to the ionized noble gas combination to generate lower-ionized sample compounds; applying a first bias voltage to a first collecting electrode associated with the first collecting electrode end; applying a second bias voltage to a second collecting electrode associated with the second collecting electrode end; generating over time a first time-dependent current at the first collecting electrode end from interaction with the high-ionized sample compounds, and generating over time a second time-dependent current at the second collecting electrode end from interaction with the lower-ionized sample compounds. The method of use is completed by displaying or visually representing to the user the first time-dependent current as a function of time and the second time-dependent current as a function of time.

The method of use may be continued by determining a time-dependent current ratio of each peak in the first time-dependent current to each peak in the second time-dependent current, each time-dependent current ratio indicative of the ionization potential of the constituent associated with the each peak, and displaying or visually representing to the user a visual representation of the time-dependent current ratio.

Additionally, the structure may be used in connection with a method to identify separated constituents in a carrier gas. The method includes the steps of:
  a. flowing the separated constituents in a carrier gas through the column gas inlet into an enclosed elongated chamber having a chamber first end, a chamber second end, and an outlet,
  b. first ionizing those constituents by a first ionization source, positioned between the column gas inlet and the chamber first end, such as by interaction with a first discharge gas ionized by the first ionization source,
  c. applying a first bias voltage to a first collecting electrode having a first collecting electrode end positioned between the column gas inlet and the outlet,
  d. generating over time a first time-dependent current at the end of the first collecting electrode from interaction with said constituents ionized by interaction with the first discharge gas ionized by the first ionization source, e. secondly ionizing the constituents by a second ionization gas, positioned between the end of the first collecting electrode and the chamber second end, ionized by a second ionization source,
f. applying a second bias voltage to the second collecting electrode having a second collecting electrode end positioned between the end of the first collecting electrode and the outlet,
g. generating over time a second time-dependent current at the end of a second collecting electrode from interaction with said constituents ionized by interaction with the second discharge gas ionized by the second ionization source,
h. flowing the separated constituents in the carrier gas out of the enclosed elongated chamber at the outlet, where the outlet is positioned between the end of the second combined collecting electrode and the second ionization source, and
i. displaying or visually representing to the user, whether on a computer display or printout, a visual representation of the first time-dependent current as a function of time and said second time-dependent current as a function of time.

The method may further include:
j. determining a time-dependent current ratio of each peak in the first time-dependent current to each peak in the second time-dependent current, and
k. displaying or visually representing to the user a visual representation of that time-dependent current ratio as a function of ionization potential, whether on a computer display or printout.

In those additional steps, each time-dependent current ratio is indicative of the ionization potential or the constituent associated with each peak.

As provided above, the first ionization source 112 may comprise a first pair of spaced-apart discharge electrode tips 124 positioned sufficient for spark formation therebetween for pulsed discharge or may comprise a lamp. Similarly, the second ionization source may comprise a second pair of spaced-apart discharge electrode tips 126 positioned sufficient for spark formation therebetween for pulsed discharge, or a lamp, for radiation of less phonotic energy that the first ionization source.

The terms and expressions which have been employed in the foregoing specification are used therein as terms of description and not of limitation, and there is no intention, in the use of such terms and expressions, of excluding equivalents of the features shown and described or portions thereof.

We claim:

1. A dual ionization source ionization detector body comprising:
   an enclosed elongated chamber,
      said enclosed elongated chamber having a chamber first end and a chamber second end;
   a first ionization source,
      said first ionization source positioned in said enclosed elongated chamber adjacent said chamber first end,
   a column gas inlet piping into said enclosed elongated chamber between said first ionization source and said chamber second end;
   a second ionization source,
      said second ionization source positioned in said enclosed elongated chamber adjacent said chamber second end,
   an outlet piping from said enclosed elongated chamber positioned between said column gas inlet piping and said second ionization source;
   a first combined bias/collecting electrode having a first combined bias/collecting electrode end exposed to said enclosed elongated chamber between said column gas inlet piping and said outlet piping; and
   a second combined bias/collecting electrode having a second combined bias/collecting electrode end exposed to said enclosed elongated chamber between said first combined bias/collecting electrode end and said second ionization source.

2. The dual ionization source ionization detector body of claim 1, wherein:
   said first ionization source comprises a first pair of spaced-apart discharge electrode tips,
      said first pair of spaced-apart discharge electrode tips positioned sufficient for spark formation therebetween within said enclosed elongated chamber for pulsed discharge.

3. The dual ionization source ionization detector body of claim 1, further comprising:
   a first discharge gas inlet into said enclosed elongated chamber proximate said chamber first end;
   a second discharge gas inlet into said enclosed elongated chamber proximate said chamber second end;
   and wherein:
   said first ionization source comprises a first pair of spaced-apart discharge electrode tips,
      said first pair of spaced-apart discharge electrode tips positioned sufficient for spark formation therebetween within said enclosed elongated chamber for pulsed discharge; and
   said second ionization source comprises a second pair of spaced-apart discharge electrode tips,
      said second pair of spaced-apart discharge electrode tips positioned sufficient for spark formation therebetween within said enclosed elongated chamber for pulsed discharge.

4. The dual ionization source ionization detector body of claim 3, wherein said outlet piping is positioned between said second combined bias/collecting electrode end and said second pair of spaced-apart discharge electrode tips.

5. The dual ionization source ionization detector body of claim 4, wherein said enclosed elongated chamber further comprises:
   a first ionization chamber section, a reaction chamber section and a second discharge chamber section, said enclosed elongated chamber having an enclosed elongated chamber longitudinal axis;
   said first discharge chamber section between said chamber first end and said column gas inlet piping,
   said first discharge chamber section having a first discharge chamber section cross sectional area perpendicular to said enclosed elongated chamber longitudinal axis;
   said second discharge chamber section between said chamber second end and said outlet piping,
   said second discharge chamber section having a second discharge chamber section cross sectional area perpendicular to said enclosed elongated chamber longitudinal axis,
   said second discharge chamber section cross sectional area equivalent to said first discharge chamber section cross sectional area;
   said reaction chamber section intermediate said first discharge chamber section and said second discharge chamber section,
   said reaction chamber section having a reaction chamber section cross sectional area perpendicular to said enclosed elongated chamber longitudinal axis, said reaction chamber section cross sectional area greater than said first discharge chamber section cross sectional area.

6. The dual ionization source ionization detector body of claim 5 further comprising:
   a first voltage bias source, said first voltage bias source electrically connected to said first combined bias/collecting electrode associated with said first combined bias/collecting electrode end; and
   a second voltage bias source, said second voltage bias source electrically connected to said second combined bias/collecting electrode associated with said second combined bias/collecting electrode end.

7. The dual ionization source ionization detector body of claim 5 further comprising:
   a first biasing-or-ground electrode positioned in said column gas inlet piping with an end of said first biasing-or-ground electrode at least adjacent to said enclosed elongated chamber; and
   a second biasing-or-ground electrode positioned in the outlet piping with an end of said second biasing-or-ground electrode at least adjacent to said enclosed elongated chamber.

8. The dual ionization source ionization detector body of claim 2 wherein said second ionization source comprises a glow-discharge lamp.

9. A method of identifying separated constituents in a carrier gas comprising the steps of:
   flowing from a column gas inlet said separated constituents in a carrier gas into an enclosed elongated chamber having a first end, a second end, and an outlet;
   ionizing said constituents by interaction with a first discharge gas ionized by a first ionization source;
   applying a first bias voltage to a first combined bias/collecting electrode having an end positioned between said column gas inlet and said outlet;
   generating over time a first time-dependent current at said end of said first combined bias/collecting electrode from interaction with said constituents ionized by interaction with said first discharge gas ionized by said first ionization source,
   ionizing said constituents by interaction with a second discharge gas ionized by a second ionization source;
   applying a second bias voltage to a second combined bias/collecting electrode having an end positioned between said end of said first combined bias/collecting electrode and said outlet;
   generating over time a second time-dependent current at said end of said second combined bias/collecting electrode from interaction with said constituents ionized by interaction with said second discharge gas ionized by said second ionization source;
   flowing said separated constituents in a carrier gas out of said enclosed elongated chamber at said outlet, said outlet positioned between said end of said second combined bias/collecting electrode and said second ionization source;
   displaying a visual representation of said first time-dependent current as a function of time and said second time-dependent current as a function of time.

10. The method of analyzing a sample compound in a carrier gas of claim 9 further comprising
   determining a time-dependent current ratio of each peak in said first time-dependent current to each peak in said second time-dependent current, each time-dependent current ratio indicative of the ionization potential of the constituent associated with said each peak; and
   displaying a visual representation of said time-dependent current ratio.

11. A dual ionization source ionization detector body comprising:
   an enclosed elongated chamber having a chamber first end and a chamber second end,
   a first discharge gas inlet into said enclosed elongated chamber near said chamber first end;
   a first ionization source positioned in said enclosed elongated chamber between said first discharge gas inlet and said chamber second end;
   a column gas inlet piping into said enclosed elongated chamber between said first ionization source and said chamber second end;
   a first collecting combined bias/collecting electrode end exposed to said enclosed elongated chamber between said column gas inlet piping and said chamber second end and adapted for electrical connection to a first voltage bias source and for transmittal of a first collected current;
   a second collecting electrode end exposed to said enclosed elongated chamber between said first combined bias/collecting electrode end and said second discharge gas inlet and adapted for electrical connection to a second voltage bias source and for transmittal of a second collected current;
   an outlet piping from said enclosed elongated chamber positioned in said elongated chamber between said second combined bias/collecting electrode end and said chamber second end; and
   a second ionization source positioned in said enclosed elongated chamber between said outlet piping and said chamber second end.

12. The dual ionization source ionization detector body of claim 11, wherein
   said first discharge gas inlet is positioned in said enclosed elongated chamber near said chamber first end.

13. The dual ionization source ionization detector body of claim 12, further comprising
   a second discharge gas inlet into said enclosed elongated chamber near said chamber second end; and wherein:
   said second ionization source comprises a second pair of spaced-apart discharge electrode tips,
      said second pair of spaced-apart discharge electrode tips positioned sufficient for spark formation therebetween within said enclosed elongated chamber for pulsed discharge.

14. The dual ionization source ionization detector body of claim 11, wherein said second ionization source comprises a glow-discharge lamp.

* * * * *

UNITED STATES PATENT AND TRADEMARK OFFICE
CERTIFICATE OF CORRECTION

PATENT NO. : 8,829,914 B2  Page 1 of 1
APPLICATION NO. : 13/675727
DATED : September 9, 2014
INVENTOR(S) : Stanley D. Stearns and Huamin Cai It is certified that error appears in the above-identified patent and that said Letters Patent is hereby corrected as shown below:

Claims

Column 12, line 41, In claim 5
the term "a first ionization chamber section" should be "a first discharge chamber section"

Column 14, line 23, In claim 11
the term "a first collecting combined bias/collecting electrode end" should be "a first combined bias/collecting electrode end"

Column 14, line 29, In claim 11
the term "a second collecting electrode end" should be "a second combined bias/collecting electrode end"

Signed and Sealed this
Tenth Day of November, 2015

Michelle K. Lee
*Director of the United States Patent and Trademark Office*